United States Patent [19]
Choudhary et al.

[11] Patent Number: 5,936,135
[45] Date of Patent: Aug. 10, 1999

[54] PROCESS FOR THE PREPARATION OF HYDROCARBONS

[75] Inventors: Vasant R. Choudhary; Anil K. Kinage; Tushar V. Choudhary, all of Maharashtra, India

[73] Assignee: Council of Scientific & Industrial Research, New Delhi, India

[21] Appl. No.: 08/917,347

[22] Filed: Aug. 26, 1997

[30] Foreign Application Priority Data

May 2, 1997 [IN] India ........................................ 1136/97

[51] Int. Cl.[6] .............................. C07C 2/52; C07C 15/00
[52] U.S. Cl. ......................... 585/418; 585/419; 585/420; 585/407
[58] Field of Search ..................................... 585/419, 418, 585/410, 407

[56] References Cited

U.S. PATENT DOCUMENTS 4,766,265  8/1988  Desmond et al. ....................... 585/415

*Primary Examiner*—Glenn Caldarola
*Assistant Examiner*—Thuan D. Dang

[57] ABSTRACT

The present invention describes a process for the conversion of a lower alkane or a mixture of lower alkanes or a feed containing lower alkane(s) to aromatics or higher hydrocarbons, which comprises (i) treating a bifunctional pentasil zeolite catalyst, optionally containing one or more transition elements, having strong dehydrogenation and acid sites with a mixture of $H_2$, steam and optionally the presence of an inert gas at a gas hourly space velocity of at least about 500 $cm^3$ $g^{-1}$ $h^{-1}$ at a temperature in the range of 400°–800° C. and pressure in the range of 1–5 atm. for a period of at least 0.5 h; (ii) treating the catalyst obtained in step (i) with air or $O_2$ at a gas hourly space velocity of at least about 200 $cm^3$ $g^{-1}$ $h^{-1}$) at a temperature in the range of 400–800° C. and pressure in the range of 1–5 atm for a period of at least 0.2 h, and (iii) contacting the catalyst obtained in step (ii) with a lower alkane or mixture of lower alkanes and at least one olefin or at least one higher paraffin or both, at a gas hourly space velocity in the range of 1000–100000 $cm^3$ $g^{-1}$ $h^{-1}$ at a temperature in the range of 300°–600° C. and pressure in the range of 1–5 atm, (iv) separating the aromatics formed from the reaction mixture by known methods and if desired, (v) recycling the unconverted lower alkanes and non-aromatics to step (iii) for further conversion.

25 Claims, No Drawings

PROCESS FOR THE PREPARATION OF HYDROCARBONS

FIELD OF THE INVENTION

This invention relates to an improved process for the conversion of lower alkane(s) to aromatics or higher hydrocarbons under non-oxidative conditions and low temperature. This invention particularly relates to an improved catalytic process for the direct conversion of methane or ethane or a mixture thereof or a hydrocarbon feed containing such alkanes to aromatics or higher hydrocarbons at low temperatures by employing, at least one olefin and/or at least one higher paraffin in the feed, in the presence of a bifunctional zeolite catalyst having dehydrogenation and acid functions. The process of the present invention could be used in petroleum and petrochemical industries for producing aromatic hydrocarbons from a feed stock comprising a lower alkane or mixture of lower alkanes such as natural gas, bio gas and olefins and/or higher paraffins.

BACKGROUND OF THE INVENTION

Methane is the major constituent of natural gas and also of biogas. World reserves of natural gas are constantly being upgraded and more natural gas is currently being discovered than oil. Because of the problems associated with transportation of a very large volumes of natural gas, most of the natural gas produced along with oil, particularly, at remote places, is flared and hence wasted. The conversion of alkanes contained in the natural gas directly to higher hydrocarbons and aromatics is extremely difficult. If technologies are made available for the conversion of the natural gas to easily transportable less volatile value added products such as aromatic hydrocarbons, a far reaching economic impact can be achieved which will also lead to exploration of more gas-rich field increasing the natural gas reserves.

Aromatic hydrocarbons are an important commodity in the petroleum and petrochemical industries. The most commercially important aromatics are benzene, toluene, ethylbenzene and xylenes. Aromatics are currently produced by catalytic reforming of various petroleum feed stocks and catalytic cracking of naphthas. Aromatics can also be produced by catalytic conversion of alcohols (particularly methanol), olefins or lower alkanes (particularly propane, butanes or LPG). The catalyst used in these processes (methanol-to-gasoline Mobil's MTG process, olefins-to-gasoline-and-distillate or MOGD or M2 forming, both developed by Mobil Oil, and LPG-to-aromatics conversion process or Cyclar Process developed by UOP) belong to the pentasil zeolite family, particularly that having ZSM-5 structure.

Oxidative Activation of Methane for its Conversion to Aromatics

An oxidative activation of methane for converting it directly to $C_2$-hydrocarbons, ethane and ethylene, is known in the prior art and it is described in a book {E. E. Wolf "Methane Conversion by Oxidative Process: Fundamental and Engineering Aspects" Van Nostrand Trinhold Catalysis Series, New York, (1992)} and also in a number or review articles {J. R. Aderson, Appl. Catal., 47 (1989) 177; J. S. Lee et. al., Catal. Rev. -Sci. Eng., 30 (1988) 249; G. J. Hutchings et. al., Chem. Soc. Rev., 18 (1989) 25; J. H. Lunsford, Catal. Today 6 (1990) 235; J. H. Lunsford, Angew. Chem. Intl. Ed. Engl. 34 (1995)}.

According to a recent U.S. Pat. No. 5,336,825 (1984) of Choudhary V. R. and co-workers, methane can be converted to gasoline range hydrocarbons comprising aromatic hydrocarbons by carrying out the conversion of methane in the following two steps. Step (i): Catalytic oxidative conversion of methane to ethylene and minor amounts of $C_3$ and $C_4$ olefins in presence of free oxygen using a basic solid catalyst at a temperature preferably between 600° C. and 850° C. Step (ii): catalytic conversion of ethylene and higher olefins formed in the step (i) to liquid hydrocarbons of gasoline range over an acidic solid catalyst containing high silica pentasil zeolite, using product stream of the step (I) as the feed.

In the other multistep processes as described in Eur, Pat. Appln. EP 516,507 (1992) and Fr. Appl. 91/6,195 (1991), a methane rich fraction of natural gas is selectively oxidized, mixed with a $C_{2+}$ hydrocarbon rich natural gas fraction, pyrolized and then the mixture is aromatized with a catalyst based on zeolite and gallium.

All the prior art teach the process for the oxidative activation of methane involves the following undesirable highly exothermic methane combustion reactions:

$$CH_4 + 2O_2 \rightarrow CO_2 + 2H_2O \qquad (1)$$

$$CH_4 + 1.5O_2 \rightarrow CO + 2H_2O \qquad (2)$$

Hence, these processes are hazardous in nature. Moreover, in these processes, undesirable carbon oxides, CO and $CO_2$, are formed thus reducing the product selectivity and also creating environmental pollution problems.

Non-oxidative Activation of Methane for its Conversion to Aromatics

High temperature non-.oxidative conversion of methane to $C_{2+}$ hydrocarbons is known in the prior art.

It has been known for a long time that methane and natural gas can be pyrolytically converted to benzene at temperatures above 899° C. (1659° F.), preferably above 1200° C.

A paper on "High Temperature Synthesis of Aromatics Hydrocarbons from Methane" published in Science 153 (1966) 1393 disclosed that aromatic hydrocarbons can be prepared from methane by contact with silica at 1000° C. The yield of hydrocarbons was in the range of 4.8–7.2% based on the methane used in the single pass at a gas space velocity of 1224 $h^{-1}$.

More recent, a non-oxidative activation of methane by the dehydrogenative coupling of methane over active carbon at temperature $\geq 1100°$ C. has been reported by H. Yagita et. al. {H. Yagita et. al., in Environmental Catalysis, G. Centi et. al. Eds. SCI Publication, Rome, 1995, page 639–642}.

A U.S. Pat. No. 4,814,533 (1989) discloses a continuous catalytic process for the production of higher molecular weight hydrocarbons rich in ethylene or aromatics or both from lower molecular weight hydrocarbons or methane in which a lower molecular weight hydrocarbon containing gas is contacted in a reaction zone with a higher molecular weight hydrocarbon synthesis catalyst at a temperature greater than 1000° C.

A recent Japanese Patent, Jpn. Kokai Tokkyo Koho JP. 07,155,600 (1995), discloses a process for the preparation of reaction media for aromatization and preparation of aromatics from methane at high temperature. The reaction media, which is prepared by thermal decomposition of cyclohexane at 1050° C., was fed with methane at 1050° C. for 2 h to give benzene in 54.7% selectivity at 30.9% conversion.

Because of the requirement of a high temperature for the conversion of methane and also due to the extensive coke formation at the high reaction temperature, the above processes based on the non-oxidative conversion of methane are difficult to practice and hence uneconomical.

Catalytic aromatization of methane in the absence of $O_2$ using zeolite catalyst is also known in the prior art.

U.S. Pat. No. 4,727,206, GB Patent 8531687 and European Patent Application No. 0 228 267 A1 discloses the aromatization of methane by contacting with gallium loaded zeolite containing group VII B metal or metal compound as a catalyst at a temperature from 600° C. to 800° C., preferably from 650° C. to 775° C., in the absence of oxygen. However, the conversion of methane into aromatics and the yield of the aromatics reported in the examples of these patents, are very low. At a weight hourly space velocity of 1.0 and absolute pressure of 7.0 bar, the methane conversion at 675° C., 700° C. and 750° C. was 3.6 wt. %, 4.9 wt. % and 8.3 wt. %, respectively and aromatics yield was 2.0 wt. %, 2.53 wt. % and 2.95 wt. %, respectively. Because of the very low aromatics yield even at a temperature as high as 750° C., this process can not be economically practised.

A U.S. Pat. No. 5,026,937 (1991) discloses a process for the aromatization of methane using a catalyst comprising about 0.1 to about 2 wt. % gallium containing ZSM zeolite and phosphorus-containing alumina, at a gas hourly space velocity of 400–7500 $h^{-1}$ at relatively low temperature conditions. As per the illustrated example of this process, when the catalyst was contacted with a stream of 100 mole % methane at a flow rate of 1.4 $h^{-1}$ LHSV (liquid hourly space velocity) at 750° C. and at atmospheric pressure, the overall methane conversion was 3.5 mole % in the single pass, the selectivity to $C_{2+}$ hydrocarbons was 72%, and the selectivity to coke was 28%. Because of the very low methane conversion even at 750° C. and low space velocity and also due to the very high selectivity to coke, this process is not economical. Because of the extensive coke formation, this process is also difficult to practice on a commercial basis.

Although aromatization of methane at or below 600° C. temperature is desirable for making the conversion of methane-to-aromatics process commercially more feasible, the aromatization of methane alone at the low temperatures is not at all thermodynamically possible. At or below 600° C. temperature, the conversion of methane to benzene, proceeds according to following reaction,

$$6CH_4 \rightarrow C_6H_6 + 9H_2 \qquad (3)$$

and involves a very large free energy change, $\Delta G_r$. The value of $\Delta G_r$, which is greater than 48 kcal per mole of benzene formed at or below 600° C., is much larger than zero. This high thermodynamic barrier does not allow the formation of benzene from methane at the lower temperatures. Hence, for the conversion of methane to aromatics at or below 600° C., it is necessary to find ways for overcoming the thermodynamic barrier and especially for the non-oxidative conversion of methane, which is the most inert of all of the hydrocarbons, at lower temperatures.

Activation of Ethane for its Conversion to Aromatics

Ethane is a minor constituent of natural gas. Ethane can be produced by the oxidative coupling of methane which is a main constituent of natural gas. Ethane is also formed in the Cyclar LPG aromatization process developed by UOP, as an undesirable by-product to an appreciable extent {M. Guisnet et al. Appl. Catal, A:Gen 89 (1992) 1–30(a review)}. The conversion of ethane to aromatics is therefore, of great practical importance. A few processes for the aromatization of ethane are known in the prior art.

A. U.S. Patent by Chu (U.S. Pat. No. 4,120,910) discloses a process for converting ethane to liquid aromatics in the presence of crystalline aluminosilicate zeolite containing catalyst. According to this process, ethane at 1100° F. (593.3° C.) and 1 atm was passed over a Cu-Zn H-ZSM-5 zeolite (prepared by ion exchange of a synthetic $NH_4$-ZSM-5 with Cu-nitrate), at space velocity=500 $cm^3 g^{-1} h^{-1}$ at STP) to give 31.75% conversion and an aromatics yield of 19.05% and the aromatics selectivity of 60%.

A U.S. Patent by Chester and Chu (U.S. Pat. No. 4,350,835) teach the preparation of aromatic hydrocarbons by passing ethane over a crystalline zeolite catalyst containing a small amount of Ga. According to this patent, passing ethane over a mixed H-ZSM-5 and alumina catalyst at 1090° F. (588° C.) at 1 atm and space velocity 0.5 $h^{-1}$ (estimated gas hourly space velocity=about 373 $cm^3 g^{-1} h^{-1}$) for 2 h gave a 21% conversion of ethane with selectivity for aromatics of 56% and yield for aromatics of 11.8%.

A U.S. Patent by Desmond and Henry (U.S. Pat. No. 4,766,265) also discloses the conversion of ethane to aromatic hydrocarbons in the presence of Ga/ZSM-5 or ZSM-11 zeolite catalyst promoted with Re and Ni, Pd, Pt, Rh or Ir at 500°–700° C. According to this patent, passing ethane over a Ga-exchanged H-ZSM-5 zeolite containing 0.6% Re and 0.3% Rh at 640° C. and space velocity of 0.73 $h^{-1}$ (estimated gas hourly space velocity=about 545 $cm^3 g^{-1} h^{-1}$) gave 48.3% ethane conversion and 60% and 29% selectivity and yield, respectively, for the hydrocarbon containing 6 or more carbon atoms.

A European Patent by Bennett and Hall (Eur. Pat. Appl. EP 202,000) also discloses a process for the aromatization of ethane over 0.1–10% Ga loaded zeolite. According to this process, ethane was passed over a Ga-impregnated MFI zeolite at 625° C., 4.5 bar and space velocity of 1.0 $h^{-1}$ (estimated gas hourly space velocity=about 747 $cm^3 g^{-1} h^{-1}$) to give 37% ethane conversion, 20% yield of aromatics and 54% selectivity for aromatics.

The main disadvantages of the prior art processes for the conversion of ethane to aromatics are as follows:

(i) The prior art ethane aromatization processes operate at high temperature, generally above 600° C. At lower temperature, the ethane conversion and aromatics selectivity or yield are poor, making the process uneconomical.

(ii) The prior art ethane aromatization process operate not only at high temperature (generally above 600° C.) but also at low gas hourly space velocity (generally at less than 1000 $cm^3 g^{-1} h^{-1}$) and consequently, the productivity of aromatics is low.

(iii) The catalyst used in the prior art ethane aromatization processes is less active and selective.

In order to make ethane-to-aromatics conversion commercially attractive and economically feasible, it is necessary to develop a novel process that operates at a low temperature (at≦600° C.), preferably at about 500° C., and high gas hourly space velocity (above 1000 $cm^3 g^{-1} h^{-1}$) preferably above 3000 $cm^3 g^{-1} h^{-1}$, using a highly active and selective catalyst.

Although aromatization of ethane at low temperatures (below 600° C.) is desirable for making the ethane aromatization process commercially more feasible, the aromatization of ethane at the low temperature is severely limited by the reaction thermodynamics. For example, at 500° C. the conversion of ethane to benzene, according to following reaction, $$3C_2H_6 \rightarrow C_6H_6 + 6H_2 \quad (4)$$

involved a large free energy change, $\Delta G_r$. The value of $\Delta G_r$, for the reaction at 500° C., is 7.2 Kcal mole$^{-1}$. At 400° C., the value of $\Delta G_r$ is still very high (17.6 Kcal mole$^{-1}$). Since the $\Delta G_r$ values at the low temperatures are much larger than zero, there is a high thermodynamic barrier for the aromatization reaction. The thermodynamic barrier does not favour the formation of benzene from ethane at the lower temperature. Hence, for the aromatization of ethane at below 600° C., it is necessary to find ways for overcoming the thermodynamic barrier and also for activating ethane at the low temperatures.

The main objective of the present invention is therefore to provide an improved process for the conversion of lower alkane or mixture of lower alkanes such as methane, ethane or their mixtures into aromatics or higher hydrocarbons under non-oxidative conditions and at a low temperature.

Another objective of the present invention is to provide an improved process for the conversion of lower alkane or mixture of lower alkanes at a temperature between 300° C. to 600° C. at a high gas hourly space velocity of 1000–100,000 cm$^3$.g$^{-1}$.h$^{-1}$ which still overcomes the thermodynamic barrier.

Yet another objective of the present invention is to provide an improved process for the conversion of lower alkane or a mixture of lower alkanes to aromatics with high conversion (above 20%), high selectivity (above 70%), and high productivity (above 5 g (aromatics) g$^{-1}$(catalyst)h$^{-1}$).

The process of the present invention has been developed on the basis of our findings that in the presence of pre-treated bifunctional zeolite catalyst having dehydrogenation and acidic properties and in the presence of at least one olefin and/or at least one higher paraffin at a space hourly velocity in the range of 1000 to 100000 cm$^3$.g$^{-1}$.h$^{-1}$ the conversion of the lower alkanes into aromatics or higher hydrocarbons takes place at a temperature in the range of 300°–600° C., and yet overcomes the thermodynamic barrier. The conversion under the above said conditions is found to be very high (above 20%) with high selectively (above 70%).

The conversion of methane and/or ethane at low temperatures in the process of the present invention can be explained by the hydrogen-transfer and/or alkylation reactions between methane or ethane or both and the olefin over the bifunctional zeolite, involving the following elementary reaction steps.

The olefin interacts with zeolitic proton to form a carbenium ion.

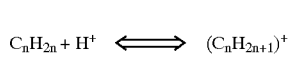

(5)

where n≧2, H$^+$=zeolitic proton or protonic acid site and $(C_nH_{2n+1})^+$ is a carbenium ion. The methane and ethane molecule is partially activated on the non-framework Ga-oxide species, as follows:

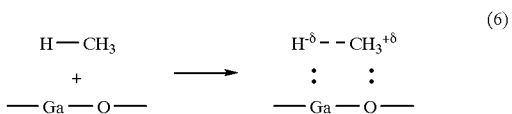

(6)

The partially activated methane molecule, $CH_3^{+\delta}$—$H^{-\delta}$, interacts with the carbenium ion to form a carbonium ion, which is a pentacoordinated carbocation, as follows:

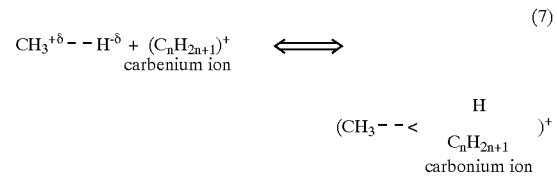

(7)

The carbonium ion, which is an ionic reaction intermediate, is decomposed to $CH_3^+$ (carbenium ion) and $C_nH_{2n+2}$, and involves a hydrogen transfer reaction between methane/ethane and the carbenium ion, or forms $CH_3$—$C_nH_{2n+1}$ with the concurrent release of a proton, H$^+$, involving an alkylation reaction between methane and the carbenium ion, as follows:

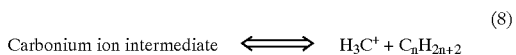

(8)

(9)

The carbocations: carbenium ions, which are trivalent classical cations, and carbonium ions, which are non-classical penta or tetracoordinated cations, are described well in the chemistry literature (G. A. Olah, Carbocations and Electrophilic Reactions, Verlag Chemie, John Wiley & Sons, 1974; Angew. Chem. Int. Ed. vol. 34, page 1393, 1995).

The methylinium ion, H$_3$C$^+$, formed in reaction 8 is rapidly decomposed and releases the proton and CH$_2$ radical; the latter is rapidly dimerized to ethene,

(10)

(11)

Because of its very high reactivity, the higher paraffin formed in reaction 8 and 9 undergoes fast dehydrogenation over the bifunctional zeolite, converting it to olefin.

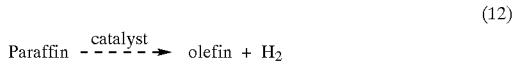

(12)

The ethane and higher olefins are oligomerized and then dehydrocyclized to aromatics over the bifunctional zeolite catalyst, as follows:

(13)

Non-oxidative Activation of Methane for its Conversion to Aromatics

The methane activation due to the presence of higher paraffin also involves the above reactions but the paraffin is first converted to olefin by reaction 12

Because of the involvement of a very high free energy change, $\Delta G_r > 48$ kcal/mole of benzene, according to reaction 3, the direct formation of benzene from methane at $\leq 600°$ C. is not possible thermodynamically. The thermodynamic barrier is, however, drastically reduced or even eliminated because of the addition of olefins or higher paraffins; the value of $\Delta G_r$, approaches to zero or even becomes negative, depending upon the additive, its concentration relative to that of methane, and temperature.

The low temperature activation of ethane occurs because of hydrogen-transfer and/or alkylation reactions between ethane and olefins over the bifunctional zeolite, involving following elementary reaction steps.

The olefin interacts with a zeolitic proton to form a carbenium ion.

(14)

where $n \geq 2$, $H^+$=zeolite proton or protonic acid site and $(C_nH_{2n+1})^+$ is a carbenium ion. The ethane molecule is partially activated on the non-framework Ga-oxide species, as follows:

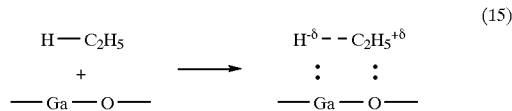
(15)

The partially activated ethane molecule, $C_2H_5^{+\delta}-H^{-\delta}$, interacts with the carbenium ion to form a carbonium ion, which is a pentacoordinated carbocation, as follows:

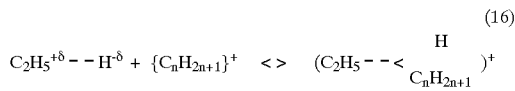
(16)

The carbonium ion, which is an ionic reaction intermediate, is decomposed to $C_2H_5^+$ carbenium ion and $C_nH_{2n+2}$, and involves a hydrogen transfer reaction between ethane and the carbenium ion, or forms $C_2H_5-C_nH_{2n+1}$ with a release of proton, $H^+$, involving an alkylation reaction between ethane and the carbonium ion, as follows:

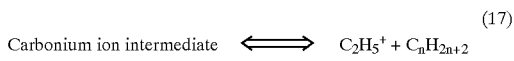
(17)

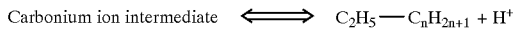
(18)

The carbocations: carbenium ions, which are trivalent classical cations, and carbonium ions, which are non-classical penta or tetracoordinated cations, are described well in the chemistry literature (G. A. Olah, Carbocations and Electrophilic Reactions, Verlag Chemie, John Wiley & Sons, 1974; Angew. Chem. Int. Ed. vol. 34, page 1393, 1995).

The carbenium ion, $C_2H_5^+$, formed in reaction 5 is rapidly decomposed to ethylene with a release of the proton.

$$C_2H_5^+ \rightarrow C_2H_4 + H^+ \qquad (19)$$

Because of its very high reactivity, the higher paraffin formed in reaction 17 (when n>2) or 18 undergoes fast dehydrogenation over the bifunctional zeolite, converting it to olefin.

(20)

The ethylene and higher olefins are oligomerized and then dehydrocyclized to aromatics over the bifunctional zeolite catalyst, as follows:

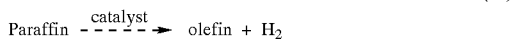
(21)

The ethane activation due to the presence of higher paraffin in the feed also involves the above reactions 14–21 but the paraffin is first converted to olefin by reaction 20.

Because of the involvement of high free energy change, $\Delta G_r > 7.2$ kcal/mole of benzene, according to reaction 4, the direct formation of benzene from ethane at $\geq 500°$ C. is not possible thermodynamically. The thermodynamic barrier is, however, drastically reduced or even eliminated because of the presence of olefins and higher paraffins in the feed; the value of $\Delta G_r$ approaches to zero or even becomes negative, depending upon the reaction temperature and the olefins and higher paraffins present in the feed and their concentration relative to that of ethane.

SUMMARY OF THE INVENTION

It has now been found by the present inventors due to exclusive research work that, by adding at least one olefin or at least one higher paraffin or both to lower alkane or mixture of lower alkanes or a feed of natural gas containing lower alkanes in the presence of a pre-treated bifunctional zeolite catalyst, having strong dehydrogenation and acid sites, the thermodynamic barrier for the aromatization of the lower alkane is overcome and the non-oxidative activation of lower alkanes occurs at or below 600° C. temperature.

Accordingly the lower alkanes can be converted to aromatics and/or higher hydrocarbons with high conversion and selectivity. Simultaneously with such conversion, the other hydrocarbons present in the feed also get converted to aromatics and/or higher hydrocarbons alkanes at the low temperature. The low temperature non-oxidative conversion of the lower alkanes results from hydrogen transfer and/or alkylation reaction of the lower alkane with the olefin, or higher paraffin present in the feed, over the catalyst. The term "lower alkanes" means the alkanes containing one or two carbon atoms. The higher hydrocarbons are the hydrocarbons containing more than two carbon atoms. The higher paraffin means the paraffin containing more than two carbon atoms.

The main products of the process of this invention are aromatic hydrocarbons comprising benzene, toluene, ortho-xylene, meta-xylene, para-xylene, ethylbenzene, trimethylbenzenes and other aromatics containing 9 and 10 carbon atoms. The minor products of the process of this invention are olefins and paraffins containing 2–4 carbon atoms, along with traces of $C_{5+}$ aliphatic hydrocarbons.

DETAILED DESCRIPTION OF THE INVENTION

Accordingly the present invention provides an improved process for the conversion of lower alkane or a mixture of lower alkanes or a feed containing lower alkane(s) to higher alkanes or aromatics which comprises.

i) treating a bifunctional pentasil zeolite catalyst optionally containing one or more transition elements, having strong dehydrogenation and acid sites, with a mixture of $H_2$, steam and optionally in the presence of an inert gas at a gas hourly space velocity of about at least 500 $cm^3 \, g^{-1} \, h^{-1}$ at a temperature in the range of 400°–800° C. and pressure in the range of 1–5 atm for a period of at least 0.5 h, ii) treating the catalyst obtained in step (i) with air or $O_2$ at a gas hourly space velocity of at least 200 $cm^3 \, g^{-1} \, h^{-1}$ at a temperature in the range of 400°–800° C. and pressure in the range of 1–5 atm for a period of at least 0.2 h, and iii) contacting the catalyst obtained in step (ii) with a lower alkane or mixture of lower alkanes and at least one olefin or at least one higher paraffin or both, at a gas hourly space velocity in the range of 1000–100000 $cm^3 \, g^{-1} \, h^{-1}$, at a temperature in the range of 300° C.–600° C. and pressure in the range of 1–5 atm, iv) separating the higher hydrocarbons/aromatics formed from the reaction mixture by known methods and if desired, v) recycling the reaction mixture containing unconverted lower alkanes and non-aromatics to step (iii) for further conversion.

The bifunctional pentasil zeolite which may be employed in the process of the present invention may have ZSM-5, ZSM-8 or ZSM-11 type crystal structure consisting of a large number of 5-membered oxygen-rings, i.e., pentasil rings, which are more stable as compared to other 0-rings. The zeolite with ZSM-5 type structure is the more preferred catalyst.

The ZSM-5, ZSM-8 and ZSM-11 type zeolite structures are all well known in the prior art and have unique shape-selective behaviour. Zeolite ZSM-5 is described in greater detail in U.S. Pat. No. 3,702,886. ZSM-11 zeolite is described in U.S. Pat. No. 3,709,979. ZSM-8 zeolite is described in Netherlands Patent 7,014,807 and U.S. Pat. No. 3,700,585. ZSM-5/ZSM-11 intermediate zeolite structure are described in U.S. Pat. No. 4,229,424. The term "Zeolite" used herein is not only for microporous crystalline alumi-nosilicate but also for microporous crystalline galloalumi-nosilicates and gallosilicates.

The bifunctional pentasil zeolite catalyst used may be preferably selected from the group consisting of Ga-containing ZSM-5 type zeolites such as Ga-impregnated H-ZSM-5, Ga-exchanged H-ZSM-5, H-gallosilicate of ZSM-5 type structure and H-galloaluminosilicate of ZSM-5 type structure. These zeolites can also be prepared by methods known in the prior art.

The bifunctional Ga-containing ZSM-5 type pentasil zeolite used in the process of present invention contains tetrahedral aluminium and/or gallium, which are present in the zeolite framework or lattice, and octahedral gallium, which is not present in the zeolite framework but present in the zeolite channels in a close vicinity of the zeolitic protonic acid sites, which are attributed to the presence of tetrahedral aluminium and gallium in the zeolite. The tetrahedral or framework Al and/or, Ga is responsible for the acid function of the zeolite and the octahedral or non-framework Ga is responsible for the dehydrogenation function of the zeolite.

The most effective and efficient bifunctional pentasil zeolite which can be used in the process of the present invention is H-galloaluminosilicate of ZSM-5 type structure having framework (tetrahedral) Si/Al and Si/Ga mole ratio of about 10–100 and 15–150, respectively, and non-framework (octahedral) Ga of about 0.5–5.0 wt. %. These pentasil H-galloaluminosilicate zeolite can be prepared by procedures known in the prior art.

The transition elements if present in the catalyst is selected from Cr, Mo, Fe, Co, Ni, Zn, Re, Ru, Rh, Pd, Os, Ir and Pt. If such elements are present these may be from trace to 10 wt. %.

The treatment of the catalyst with the mixture of $H_2$, steam and inert gas if necessary in step (i) is essential. Because of this dehydrogenation treatment, sites in the vicinity of zeolite protonic acid sites in the zeolite are created due to the uniform dispersion of the metal oxide present in the catalyst. The inert gas if used may be selected from $N_2$, He, Ar etc. The inert gas in step (i) is used to dilute the $H_2$—steam mixture. The treatment step in (ii) of the catalyst obtained in step (i) with air or $O_2$ is also essential for effecting the dehydrogenation activity. In the treatment step (i), the $H_2$/inert gas and steam/inert gas ratios may be in the range of 0.05–5.0 and 0.02–2.0, respectively.

When pentasil H galloaluminosilicate zeolites are used, the density of strong acid sites can be controlled by the framework Al/Si mole ratio, the higher the Al/Si ratio, the higher is the density of strong acid sites. The highly dispersed non-framework gallium oxide species can be obtained by the degalliation of the zeolite by its pretreatment with $H_2$ and steam. The zeolite containing strong acid sites with high density and also highly dispersed non-framework gallium oxide species in close proximity of the zeolite acid site is preferred for the process of the present invention. The catalyst may or may not contain any binder such as alumina, silica or clay material. The catalyst can be used in the form of pellets, extrudates and particles of different shapes and sizes.

In the process of this invention, the feed comprising lower alkanes, olefins and/or higher paraffins may be contacted with the catalyst in a single or multiple fixed bed reactors, fluid bed reactor or moving bed reactor, known in the prior art.

The olefins in the feed may be selected from olefins containing 2–10 carbon atoms more preferably 2–4 carbon atoms. The preferred higher paraffin in the feed may be selected from paraffins containing 2–10 carbon atoms more preferably 3–6 carbon atoms. The concentration of inert gas $N_2$ if present in the feed may be from traces to 80 mole %; the preferred mole ratio of olefin and/or higher paraffin to methane and/or ethane in the feed ranges from about 0.2 to about 2.0; the preferred gas hourly space velocity of the feed ranges from about 3000 cm$^3$ g$^{-1}$ h$^{-1}$ to about 50,000 cm$^3$ g$^{-1}$ h$^{-1}$; the preferred temperature ranges from 400° C. to 600° C.; and the preferred pressure ranges from above 1 atm to about 3 atm.

In a preferred embodiment of the process of this invention, using a feed comprising 33.3 mole % $CH_4$, 16.7 mole % iso-butene and 50 mole % $N_2$, the methane and iso-butene present in the feed can be converted to aromatics with 44.2% and 100%, respectively, conversion and 93.8% selectivity for aromatics with less than 1% selectivity for coke at 500° C., and gas hourly space velocity of 6200 cm$^3$ g$^{-1}$ h$^{-1}$ and pressure of 1.1 atm.

Various terms used in this specification have the following meanings.

Framework Si means Si present in the lattice of the zeolite.
Framework Al or Ga means the Tetrahedral Al or Ga present in the lattice of the zeolite.
Non-framework Ga means Octahedral Ga present in the zeolite channels.
Gas hourly space velocity, (GHSV) means volume of feed gases, measured at 0° C. and 1 atm pressure passed over a unit mass of catalyst per hour.
Conversion, % means weight percent of a particular reactant converted to all the products.
Product Selectivity, %={(weight percent of reactant or reactants converted to a particular product)/(weight product of reactant or reactants converted to all products)}X 100.
Conversion given in the examples is per pass conversion.

The present invention is described with reference to the examples given below which are provided to illustrate the invention only and therefore, should not be construed to limit the scope of the invention.

EXAMPLES 1–8

These examples illustrate the catalytic process of the present invention for the low temperature non-oxidative conversion of methane and thereby converting it directly to higher hydrocarbons or aromatics using n-butene or iso-butene or propene or ethene or propane or n-hexane as an additive in the feed comprising methane, and using ZSM-5 type H-galloaluminosilicate zeolite having bulk Si/Ga=24.3, bulk Si/Al=40.3, framework Si/Ga=49.9, framework Si/Al=40.3, Na/(Al+Ga)=0.03, non-framework Ga=0.32 mmol g$^{-1}$, crystal morphology or shape=spherical-hexagonal, crystal size=5.5±1.5 μm and strong acid sites measured in terms of pyridine chemisorbed at 400° C.=0.46 mmol g$^{-1}$. All the ratio are mole ratios. The zeolite was prepared by the process described in European Patent Application EP 0124271 and in the reference: Choudhary et. Al. J. Catal. 158 (1996) 23.

A conventional tubular quartz reactor of 12 mm internal diameter packed with the zeolite catalyst of 52–72 mesh size particles and kept in the tubular electrical furnace such that the catalyst is in a constant temperature zone of the furnace, was used for illustrating the process. The zeolite catalyst packed in the reactor was pre-treated in a flow of $H_2$—steam—$N_2$ mixture with $H_2/N_2$ and steam/$N_2$ mole ratio of 2.0 and 0.05, respectively, at a GHSV of 1050 cm$^3$ g$^{-1}$ h$^{-1}$ at 550° C. for 1 h and then in a flow of air with a GHSV of 1050 cm$^3$ g$^{-1}$ h$^{-1}$ at 550° C. for 1 h. The catalytic process is carried out by passing continuously a mixture of methane and $N_2$ with or without a hydrocarbon additive, such as n-butene or iso-butene or propene or ethene or propane or n-hexane in the feed over the pre-treated zeolite catalyst at different process conditions given in Table 1. The concentration of methane in the feed for all experimental runs was 33.3 mol %. The reactor or reaction temperature was measured by Chromel-Alumel thermocouple located axially in the catalyst bed. The hydrocarbons in the feed and in the products of the reaction were analysed by an on-line gas chromatograph with a flame ionized detector and computing integrator, using a 3 mm×3 m Poropak-Q column for separating $C_1$–$C_4$ hydrocarbons and using a 3 mm×5 m column containing 5% Benton-34-5% dinonyphthalate on chromosorb-W for separating aromatic hydrocarbons.

The conversion and aromatics selectivity data were obtained from the feed and product composition, as follows: conversion (%)={(wt. % of reactant in the feed hydrocarbons—wt. % of reactant in the product hydrocarbons)/(wt. % of reactant in the feed hydrocarbons)}×100 and aromatic selectivity (%)={wt. % of the aromatics in the hydrocarbon products)/(100–wt. % of reactants in the hydrocarbon products)}×100.

The results at different process conditions are presented in Table 1. The conversion of methane and other hydrocarbon reactants to coke formed on the catalyst was 1.0%.

TABLE 1

Results of the catalytic reactions, Feed = a mixture of $CH_4$ (33.3 mole %) and $N_2$ with or without olefinic or higher paraffinic hydrocarbon additive, A.

| | Example No. | | | | | | | |
|---|---|---|---|---|---|---|---|---|
| | 1 | 2 | 3 | 4 | 5 | 6 | 7 | 8 |
| Reaction conditions | | | | | | | | |
| Additive in feed | None | None | n-butene | i-butene | propene | ethene | propane | n-hexane |
| A/$CH_4$ mole ratio | 0.0 | 0.0 | 0.46 | 0.43 | 0.83 | 1.05 | 0.68 | 0.83 |
| GHSV (cm$^3$ g$^{-1}$ h$^{-1}$) | 3100 | 6200 | 3100 | 6200 | 6200 | 6200 | 3100 | 3100 |
| Temperature (° C.) | 600 | 600 | 600 | 500 | 500 | 600 | 60& | 600 |
| Pressure (atm) | 1.1 | 1.1 | 1.1 | 1.1 | 1.1 | 1.1 | 1.1 | 1.1 |
| Distribution of hydrocarbons in products (wt %) | | | | | | | | |
| $CH_4$ | 100 | 100 | 21.1 | 22.2 | 20.6 | 21.9 | 38.6 | 13.9 |
| $C_2H_4$ | — | — | 2.8 | 0.9 | 1.1 | 1.5 | 3.8 | 1.6 |
| $C_2H_6$ | — | — | 1.1 | 0.6 | 0.6 | 1.1 | 2.1 | 2.4 |
| $C_3H_6$ | — | — | 1.3 | 0.6 | 0.6 | 0.1 | 2.9 | 0.6 |

TABLE 1-continued

Results of the catalytic reactions, Feed = a mixture of CH$_4$ (33.3 mole %) and N$_2$ with or without olefinic or higher paraffinic hydrocarbon additive, A.

| | Example No. | | | | | | | |
|---|---|---|---|---|---|---|---|---|
| | 1 | 2 | 3 | 4 | 5 | 6 | 7 | 8 |
| C$_3$H$_8$ | — | — | 1.0 | 2.3 | 4.3 | 3.2 | 5.0 | 0.8 |
| C$_4$H$_8$ | — | — | 0.0 | 0.0 | 0.1 | 0.1 | 0.0 | 0.0 |
| C$_4$H$_{10}$ | — | — | 0.2 | 0.5 | 0.5 | 0.3 | 0.1 | 0.0 |
| C$_{5+}$ aliphatics | — | — | 0.0 | 0.0 | 0.0 | 0.0 | 0.0 | 0.0 |
| Benzene | — | — | 18.1 | 11.8 | 16.6 | 17.6 | 15.1 | 29.0 |
| Toluene | — | — | 34.7 | 34.9 | 35.8 | 33.9 | 16.9 | 35.9 |
| Ethylbenzene & p-xylene | — | — | 3.6 | 5.8 | 4.5 | 4.0 | 2.7 | 2.5 |
| m-xylene | — | — | 10.4 | 16.5 | 12.1 | 11.4 | 6.7 | 6.8 |
| o-xylene | — | — | 0.1 | 0.1 | 0.1 | 0.2 | 0.0 | 0.0 |
| C$_9$—C$_{10}$ aromatics | — | — | 5.6 | 3.8 | 3.1 | 4.7 | 6.1 | 6.5 |
| Total hydrocarbons | 100 | 100 | 100 | 100 | 100 | 100 | 100 | 100 |
| Conversion of CH$_4$ (%) | 0.0 | 0.0 | 45.0 | 44.2 | 34.7 | 36.3 | 12.0 | 24.1 |
| Conversion of A (%) | — | — | 100 | 100 | 99.7 | 98.8 | 91.1 | 100 |
| Selectivity for aromatics (%) | — | — | 92.0 | 93.8 | 91.8 | 93.8 | 84.2 | 93.8 |

The results in the Table 1 clearly show that in the absence of olefin or higher paraffin in the feed, the conversion of methane in the process is zero and hence there is no conversion of methane at 600° C. and consequently below 600° C. But when an olefin and a higher paraffin are added to the feed, the thermodynamic barrier is overcome and the methane from the feed is activated at 500°–600° C. and thereby it is converted to higher hydrocarbons or aromatics with high conversion and high selectivity for aromatics. The hydrocarbon additive from the feed is also converted to aromatics with very high conversion, reaching as high as 100% conversion.

EXAMPLES 9–19

These examples illustrate the influence of process conditions such as olefin/methane mole ratio in the feed, reaction temperature and gas hourly space velocity, GHSV, on the product distribution, on the conversion of methane and olefin present in the feed and also on the selectivity for aromatics in the process of this invention.

The catalytic process was carried out by the procedures described in EXAMPLES 1 to 8 and also using the same catalyst and reactor described in EXAMPLES 1 to 8, except that the catalyst was pre-treated in a flow of H$_2$—steam—N$_2$ mixture with H$_2$/N2 and steam/N$_2$ mole ratio of 0.5 and 0.05, respectively, at a GHSV of 2500 cm$^3$ g$^{-1}$ h$^{-1}$ at 600° C. for 2 h and then in a flow of air with a GHSV of 2500 cm$^3$ g$^{-1}$ h$^{-1}$ at 600° C. for 0.5 h, at the process conditions given in Tables 2 and 3. In all the experiments, the concentration of methane in the feed was 33.3 mole % and the feed diluent was N$_2$.

The results show the influence of the hydrocarbon additive, methane mole ratio in the feed, reaction temperature on the distribution of hydrocarbons in hydrocarbon products, on the conversion of methane and propene or n-butene, and also on the selectivity for aromatics are presented in Table 2.

The results showing the influence of gas hourly space velocity on the performance of the process of the present invention are shown in Table 3.

TABLE 2

Results of the catalytic reactions, Feed = a mixture of CH$_4$ (33.3 mole %), N$_2$ and olefinic hydrocarbon additive, A.

| | Example No. | | | | | |
|---|---|---|---|---|---|---|
| | 9 | 10 | 11 | 12 | 13 | 14 |
| Reaction Conditions | | | | | | |
| Additive, in feed | propene | propene | propene | n-butene | n-butene | n-butene |
| A/CH$_4$ mole ratio | 1.0 | 0.8 | 0.4 | 0.5 | 0.4 | 0.4 |
| GHSV (cm$^3$ g$^{-1}$ h$^{-1}$) | 6200 | 6200 | 6200 | 6200 | 6200 | 6200 |
| Temperature (° C.) | 500 | 500 | 500 | 600 | 500 | 400 |
| Pressure (atm) | 1.1 | 1.1 | 1.1 | 1.1 | 1.1 | 1.1 |
| Distribution of hydrocarbons in products (wt %) | | | | | | |
| CH$_4$ | 15.8 | 20.6 | 37.6 | 21.1 | 25.8 | 33.7 |
| C$_2$H$_4$ | 1.6 | 1.1 | 1.3 | 33 | 1.5 | 1.5 |
| C$_2$H$_6$ | 0.6 | 0.6 | 0.4 | 0.8 | 0.6 | 0.5 |
| C$_3$H$_6$ | 1.2 | 0.6 | 0.7 | 1.6 | 0.8 | 1.9 |
| C$_3$H$_8$ | 5.4 | 4.3 | 3.4 | 1.1 | 2.7 | 3.1 |

TABLE 2-continued

Results of the catalytic reactions, Feed = a mixture of $CH_4$ (33.3 mole %), $N_2$ and olefinic hydrocarbon additive, A.

| | Example No. | | | | | |
|---|---|---|---|---|---|---|
| | 9 | 10 | 11 | 12 | 13 | 14 |
| $C_4H_8$ | 0.7 | 0.1 | 0.0 | 0.0 | 0.1 | 6.8 |
| $C_4H_{10}$ | 1.3 | 0.5 | 0.2 | 0.3 | 0.8 | 2.9 |
| $C_{5+}$ aliphatics | 0.0 | 0.0 | 0.0 | 0.0 | 0.0 | 0.0 |
| Benzene | 17.1 | 16.6 | 11.6 | 19.0 | 11.7 | 10.2 |
| Toluene | 33.7 | 35.8 | 23.8 | 35.1 | 29.3 | 23.0 |
| Ethylbenzene & p-xylene | 6.1 | 4.5 | 4.4 | 3.6 | 5.9 | 2.6 |
| m-xylene | 12.4 | 12.1 | 12.8 | 9.3 | 15.9 | 6.0 |
| o-xylene | 0.3 | 0.1 | 0.1 | 0.1 | 0.1 | 0.0 |
| $C_9$–$C_{10}$ aromatics | 3.8 | 3.1 | 3.7 | 4.7 | 4.8 | 7.8 |
| Total hydrocarbons | 100 | 100 | 100 | 100 | 100 | 100 |
| Conversion of $CH_4$ (%) | 38.0 | 34.7 | 22.3 | 43.0 | 36.4 | 15.0 |
| Conversion of A (%) | 98.4 | 99.7 | 98.7 | 100 | 99.8 | 88.8 |
| Selectivity for aromatics (%) | 88.4 | 91.8 | 91.4 | 91.0 | 91.4 | 83.6 |

TABLE 3

Results of the catalytic reactions, Feed = a mixture of $CH_4$ (33.3 mole %), $N_2$ and olefinic hydrocarbon additive, A.

| | Example No | | | | |
|---|---|---|---|---|---|
| | 15 | 16 | 17 | 18 | 19 |
| Reaction Conditions | | | | | |
| Additive, in feed A/$CH_4$ mole ratio | n-butene 0.93 | n-butene 1.1 | n-butene 1.0 | n-butene 1.0 | n-butene 1.04 |
| GHSV ($cm^3$ $g^{-1}$ $h^{-1}$) | 6200 | 12,000 | 21,000 | 42,000 | 84,000 |
| Temperature (° C.) | 500 | 500 | 500 | 500 | 500 |
| Pressure (atm) | 1.1 | 1.1 | 1.2 | 1.2 | 1.3 |
| Distribution of hydrocarbons in products (wt. %) | | | | | |
| $CH_4$ | 14.9 | 13.6 | 15.1 | 15.8 | 19.5 |
| $C_2H_4$ | 1.4 | 1.4 | 2.4 | 3.5 | 4.6 |
| $C_2H_6$ | 1.5 | 0.5 | 0.4 | 0.3 | 0.2 |
| $C_3H_6$ | 0.6 | 2.3 | 2.9 | 6.5 | 14.9 |
| $C_3H_8$ | 0.8 | 2.0 | 2.8 | 0.3 | 0.8 |
| $C_4H_8$ | 0.0 | 0.8 | 2.7 | 4.3 | 10.9 |
| $C_4H_{10}$ | 0.3 | 1.4 | 2.3 | 3.1 | 7.6 |
| $C_{5+}$ aliphatics | 0.0 | 0.0 | 0.0 | 0.0 | 0.0 |
| Benzene | 31.6 | 13.8 | 11.4 | 8.1 | 2.0 |
| Toluene | 31.2 | 40.5 | 35.8 | 32.8 | 13.8 |
| Ethylbenzene & p-xylene | 2.4 | 6.3 | 8.6 | 10.8 | 13.0 |
| m-xylene | 6.8 | 14.7 | 12.6 | 11.5 | 6.3 |
| o-xylene | 0.1 | 0.2 | 0.3 | 0.4 | 1.8 |
| $C_9$–$C_{10}$ aromatics | 8.4 | 2.5 | 2.7 | 2.6 | 4.6 |
| Total hydrocarbons | 100 | 100 | 100 | 100 | 100 |
| Conversion of $CH_4$ (%) | 36.4 | 36.4 | 32.2 | 26.8 | 7.4 |
| Conversion of A (%) | 100 | 99.0 | 96.5 | 94.5 | 86.6 |
| Selectivity for aromatics (%) | 94.7 | 91.3 | 86.9 | 82.8 | 59.8 |

EXAMPLE 20

This example illustrates the catalytic process of the present invention when no feed diluent is used. The catalytic process was carried out by the procedures described in EXAMPLES 1 to 8 and also using same catalyst and reactor described in EXAMPLES 1 to 8, except that the catalyst was pre-treated in a flow of $H_2$—steam—$N_2$ mixture with $H_2/N_2$ and steam/$N_2$ mole ratio of 4.0 and 2.0, respectively, at GHSV of 1000 $cm^3$ $g^{-1}$ $h^{-1}$ at 500° C. for 1 h and then in a flow of $O_2$ with GHSV of 500 $cm^3$ $g^{-1}$ $h^{-1}$ at 600° C. for 5 h, at the following process conditions.

Feed: A mixture of 50 mole % methane and 50 mole % n-butene.

n-Butene/$CH_4$ mole ratio: 1.0
GHSV: 13,200 $cm^3$ $g^{-1}$ $h^{-1}$
Temperature: 500° C.
Pressure : 1.1 atm The results obtained are as follows.
Conversion of methane=31.7%
Conversion of n-butene=97.2%
Selectivity for aromatics=87.3%
Productivity for aromatics=15.6 $g_{(aromatics)}/g_{(catalyst)}/h$
Distribution of hydrocarbons in products: 13.6 wt. % $CH_4$, 1.8 wt. % $C_2H_4$, 0.6 wt. % $C_2H_6$, 1.3 wt. % $C_3H_6$, 4.5 wt. % $C_3H_8$, 2.3 wt. % $C_4H_8$, 2.4 wt. % $C_4H_{10}$, 15.1 wt. % benzene, 34.7 wt. % toluene, 7.3 wt. % ethylbenzene and para-xylene, 12.2 wt. % meta-xylene, 0.4 wt. % ortho-xylene and 3.8 wt. % $C_{9\ \&\ 10}$ aromatics.

EXAMPLES 21–29

These examples illustrate the catalytic process of this invention for the low temperature activation of ethane and thereby converting it to higher hydrocarbons or aromatics using olefins and higher paraffins as additive in the feed comprising ethane, and using ZSM-5 type H-galloaluminosilicate zeolite having bulk Si/Ga=24.3, bulk Si/Al=40.3, framework Si/Ga=49.9, framework Si/Al=40.3, Na/(Al+Ga)=0.03, non-framework Ga=0.32 mmol $g^{-1}$, crystal morphology or shape=spherical-hexagonal, crystal size= 5.5±1.5 μm and strong acid sites measured in terms of pyridine chemisorbed at 400° C.=0.46 mmol $g^{-1}$. All the ratios are mole ratios. The zeolite was prepared by the process described in European Patent Application EP 0124271 and in the reference: Choudhary et al. J. Catal. 158 (1996) 23.

A conventional tubular quartz reactor of 12 mm internal diameter packed with the zeolite catalyst of 52–72 mesh size particles and kept in the tubular electrical furnace such that the catalyst is in a constant temperature zone of the furnace, was used for illustrating the process. The zeolite catalyst packed in the reactor was pre-treated in a flow of $H_2$—steam—$N_2$ mixture with $H_2/N_2$ and steam/$N_2$ mole ratio of 2.0 and 0.05, respectively, at a GHSV of 1000 $cm^3$ $g^{-1}$ $h^{-1}$ at 550° C. for 1 h and then in a flow of air with a GHSV of 1050 $cm^3$ $g^{-1}$ $h^{-1}$ at 550° C. for 1 h. The catalytic process is carried out by passing continuously a mixture of ethane and $N_2$ with or without olefinic and higher paraffinic hydrocarbon additives, designated by O and HP, respectively, in the feed over the pre-treated zeolite catalyst at different process conditions given in Table 2. The reactor or reaction temperature was measured by Chromel-Alumel thermocouple located axially in the catalyst bed. The hydrocarbons in the feed and in the products of the reaction were analysed by an on-line gas chromatograph with a flame ionized detector and computing integrator, using a 3 mm×3 m Poropak-Q column for separating $C_1$–$C_4$ hydrocarbons and using a 3 mm×5 m column containing 5% Benton-34—5% dinonyphthalate on chromosorb-W for separating aromatic hydrocarbons.

The conversion and aromatics selectivity data were obtained from the feed and product composition, as follows: conversion (%)={wt. % of reactant in the feed hydrocarbons—wt. % of reactant in the product hydrocarbons)/(wt. % of reactant in the feed hydrocarbons)}×100 and aromatic selectivity (%)={(wt. % of the aromatics in the hydrocarbon products)/(100—wt. % of reactants in the hydrocarbon products)}×100.

The results in Table 4 clearly show that in the absence of olefin and higher paraffin in the feed, the conversion of ethane in the process is very small. But when olefin and higher paraffin are added in the feed, the ethane from the feed is activated even at or below 500° C. and thereby it is converted to aromatics with high conversion and high selectivity for aromatics. The hydrocarbon additives from the feed are also converted to aromatics with very high conversion.

Table 4 illustrates that the ethane conversion is increased drastically and also the selectivity for aromatics is increased to a large extent because of the presence of higher paraffins and olefins in the feed. The hydrocarbon product distributions in the nine runs are given in Table 5.

TABLE 4

Results of aromatization of ethane and simultaneous aromatization of ethane, olefins and higher paraffins at GHSV of 6200 $cm^3$ $g^{-1}$ $h^{-1}$ and pressure of 1.1 atm. O = olefin, HP = higher paraffin, $S_{ar}$ = selectivity for aromatics, $Y_{ar}$ = yield of aromatics based on the ethane conversion.

| Ex No | Temp ° C. | Feed composition (mole %) | O/$C_2H_6$ | HP/ $C_2H_6$ | (O + HP)/ $C_2H_6$ | Conversion (%) $C_2H_6$ | olefin | higher paraffin | $S_{Ar}$ (%) | $Y_{Ar}$ (%) |
|---|---|---|---|---|---|---|---|---|---|---|
| 21 | 500 | 33% $C_2H_6$ + 67% $N_2$ | 0.0 | 0.0 | 0.0 | 0.9 | — | — | 47.9 | 0.4 |
| 22 | 500 | 33% $C_2H_6$ + 25% n-$C_4H_8$ + 7% n-$C_6H_{14}$ + 35% $N_2$ | 0.76 | 0.21 | 0.97 | 55.0 | 98.9 | 100 | 92.4 | 50.8 |
| 23 | 500 | 33% $C_2H_6$ + 29% $C_3H_6$ + 10% n-$C_6H_{14}$ + 28% $N_2$ | 0.88 | 0.30 | 1.18 | 50.1 | 99.0 | 100 | 91.6 | 45.9 |
| 24 | 500 | 33% $C_2H_6$ + 33% $C_2H_4$ + 5% $C_3H_8$ + 29% $N_2$ | 1.0 | 0.15 | 1.15 | 41.6 | 95.2 | 72.8 | 93.5 | 38.9 |
| 25 | 600 | 33% $C_2H_6$ + 67% $N_2$ | 0.0 | 0.0 | 0.0 | 11.2 | — | — | 65.1 | 7.3 |
| 26 | 600 | 33% $C_2H_6$ + 5% n-$C_4H_8$ + 15% n-$C_6H_{14}$ + 47% $N_2$ | 0.15 | 0.45 | 0.6 | 61.2 | 98.2 | 100 | 86.7 | 53.1 |
| 27 | 600 | 33% $C_2H_6$ + 33% n-$C_4H_8$ + 34% n-$C_4H_{10}$ | 1.03 | 1.0 | 2.03 | 70.0 | 99.0 | 98.5 | 88.0 | 61 |
| 28 | 400 | 33% $C_2H_6$ + 67% $N_2$ | 0.0 | 0.0 | 0.0 | 0.0 | — | — | — | 0.0 |
| 29 | 400 | 33% $C_2H_6$ + 30% n-$C_3H_6$ + 10% n-$C_6H_{14}$ + 27% $N_2$ | 0.91 | 0.3 | 1.21 | 37.4 | 95.6 | 85.1 | 86.2 | 32.2 |

TABLE 5

Hydrocarbon product distribution in Examples 21–29

| Hydrocarbon (wt %) | 21 | 22 | 23 | 24 | 25 | 26 | 27 | 28 | 29 |
|---|---|---|---|---|---|---|---|---|---|
| Methane | 0.1 | 1.2 | 1.4 | 1.5 | 1.0 | 3.4 | 3.5 | 0.0 | 0.5 |
| Ethylene | 0.4 | 1.0 | 0.8 | 2.1 | 2.7 | 3.7 | 3.2 | 0.0 | 0.6 |
| Ethane | 99.1 | 14.9 | 16.1 | 27.1 | 88.8 | 15.0 | 6.2 | 100 | 19.9 |
| Propylene | 0.0 | 0.9 | 0.4 | 1.7 | 0.2 | 1.3 | 1.9 | 0.0 | 1.8 |
| Propane | 0.0 | 2.0 | 4.0 | 2.8 | 0.0 | 1.8 | 2.5 | 0.0 | 3.8 |
| Butylenes | 0.0 | 0.5 | 0.4 | 0.3 | 0.0 | 0.2 | 0.4 | 0.0 | 4.0 |
| Butanes | 0.0 | 1.4 | 0.4 | 0.8 | 0.0 | 1.1 | 0.6 | 0.0 | 1.3 |
| $C_{5+}$ aliphatics | <0.1 | <0.1 | <0.1 | 0.1 | 0.0 | <0.1 | <0.1 | 0.0 | 4.2 |
| Benzenes | 0.2 | 17.0 | 15.9 | 12.5 | 2.6 | 27.3 | 30.3 | 0.0 | 3.8 |
| Toluene | 0.2 | 35.1 | 37.7 | 30.1 | 1.6 | 32.5 | 36.1 | 0.0 | 22.1 |
| Ethylbenzene + p-xylene | 0.0 | 7.0 | 5.3 | 5.6 | 0.0 | 2.4 | 2.7 | 0.0 | 7.8 |
| m-Xylene | 0.0 | 14.9 | 13.8 | 11.7 | 0.0 | 6.0 | 6.7 | 0.0 | 13.2 |
| o-Xylene | 0.0 | 0.4 | 0.2 | 0.2 | 0.1 | 0.1 | 0.1 | 0.0 | 1.2 |
| $C_{9+10}$ aromatics | 0.0 | 3.7 | 3.6 | 3.5 | 3.0 | 5.2 | 5.8 | 0.0 | 15.8 |
| Total | 100 | 100 | 100 | 100 | 100 | 100 | 100 | 100 | 100 |

EXAMPLE 30

This example illustrates the influence gas hourly space velocity, GHSV, on the product distribution, on the conversion of ethane, n-butylene and n-hexane present in the feed and also on the selectivity for aromatics at 500° C. in the process of this invention.

The catalytic process was carried out by the procedures described in EXAMPLES 21–29 and also using the same catalyst and reactor described in EXAMPLES 21–29, except that the catalyst was pre-treated in a flow of $H_2$—steam—$N_2$ mixture with $H_2/N_2$ and steam/$N_2$ mole ratio of 0.5 and 0.05, respectively, at a GHSV of 2500 $cm^3$ $g^{-1}$ $h^{-1}$ at 600° C. for 2 h and then in a flow of air with a GHSV of 1000 $cm^3$ $g^{-1}$ $h^{-1}$ at 600° C. for 0.5 h, at the following process conditions for step (iii):

Feed: A mixture of 33 mole % ethane, 33 mole % of n-butylene, 10 mole % of n-hexane and balance $N_2$.

GHSV: Varied from 3100 to 80150 $cm^3$ $g^{-1}$ $h^{-1}$

Pressure: 1.2±0.1 atm.

Temperature: 500° C.

The results at the different gas hourly space velocities are given in Table 6. The results show that even at very high GHSV, the conversion of ethane and other hydrocarbons is high and also the selectivity for aromatics is high and consequently the productivity of aromatics is also high.

TABLE 6

Results of simultaneous aromatization of ethane, n-butylene and n-hexane.

| | GHSV ($cm^3$ $g^{-1}$ $h^{-1}$) | | | | |
|---|---|---|---|---|---|
| | 3,100 | 12,380 | 20,980 | 40,720 | 80,150 |
| Conversion (%) | | | | | |
| Ethane | 51.5 | 41.4 | 35.8 | 26.1 | 9.0 |
| n-Butylene | 99.5 | 98.0 | 96.9 | 92.4 | 84.7 |
| n-Hexane | 100 | 99.1 | 90.1 | 82.3 | 70.2 |
| Selectivity for aromatics (%) | 90.1 | 85.6 | 84.3 | 76.1 | 56.6 |
| Yield of aromatics based on ethane conversion (%) | 46.4 | 35.4 | 30.2 | 19.9 | 5.1 |
| Hydrocarbon Product | | | | | |
| Distribution (wt %) | | | | | |
| Methane | 4.3 | 2.6 | 2.0 | 0.7 | 0.4 |
| Ethylene | 0.4 | 1.6 | 2.3 | 3.1 | 3.5 |
| Ethane | 13.0 | 15.7 | 17.0 | 19.8 | 24.4 |
| Propylene | 0.5 | 2.1 | 2.0 | }10.0 | }14.8 |
| Propane | 3.1 | 3.3 | 4.0 | | |
| Butylenes | 0.3 | 1.0 | 1.5 | 3.8 | 7.7 |
| Butanes | 0.2 | 2.4 | 2.1 | 3.5 | 7.6 |
| $C_5$ + aliphatics | <0.1 | 0.2 | 2.3 | 4.1 | 7.i |
| Benzene | 22.3 | 13.3 | 8.6 | 4.8 | 1.8 |
| Toluene | 36.5 | 35.8 | 30.4 | 22.0 | 11.0 |
| Ethylbenzene + p-xylene | 3.8 | 7.0 | 8.4 | 11.8 | 10.5 |
| m-Xylene | 11.1 | 12.0 | 16.5 | 13.2 | 5.4 |
| o-Xylene | 0.2 | 0.3 | 0.2 | 0.7 | 1.8 |
| $C_{9+10}$ aromatics | 4.2 | 2.7 | 2.7 | 2.5 | 4.0 |
| Total | 100 | 100 | 100 | 100 | 100 |

Advantages of the invention:
i) Because of the high thermodynamic barrier, the direct conversion of lower alkane aromatics or higher hydrocarbons at or below 600° C. temperature in the absence of oxygen other oxidizing agent is not possible thermodynamically. By the process of the present invention, the thermodynamic barrier is overcome and the lower alkane such as methane or ethane can be converted non-oxidatively at or below 600° C. temperature to aromatics higher hydrocarbons simultaneously with the aromatization of olefins or higher paraffins added to the feed.
ii) In the process of the invention, the catalyst used for the low temperature non-oxidation conversion is a bifunctional pentasil zeolite having both acid and dehydrogenation properties which facilitate the conversion to aromatics at low temperatures and at non oxidative conditions resulting in higher selectivity.
iii) By the process of the invention, the lower alkanes and other hydrocarbons present in the feed can be converted to aromatics with high conversion (above 20% and 80% respectively) and also with very high selectivity (above 70%) for aromatics and very low selectivity for coke (less than 1%).

iv) The process of the invention is operated not only at the low temperature but also at the high gas hourly space velocity (above 1000 $cm^3 \cdot g^{-1} \cdot h^{-3}$) and hence the productivity of aromatics is high (above 5 g. (aromatics) $g^{-1}$ (catalyst) $h^{-1}$).

v) By the process of the invention, methane which is the most inert hydrocarbon and which is difficult to activate for direct conversion to higher hydrocarbons, can be converted to aromatics at low temperatures.

vi) The process of the invention does not produce undesirable carbon oxides and is therefore is important.

We claim:

1. A process for the conversion of a $C_{1-2}$ alkane or a mixture of said alkanes or a feed containing said alkane(s) to aromatics, which comprises:

i) treating a bifunctional pentasil zeolite catalyst, optionally containing one or more transition elements, having strong dehydrogenation and acid sites with a mixture of $H_2$, steam and optionally the presence of an inert gas at a gas hourly space velocity of at least about 500 $cm^3g^{-1}h^{-1}$ at a temperature in the range of 400°–800° C. and pressure in the range of 1–5 atm for a period of at least 0.5 h;

ii) treating the catalyst obtained in step (i) with air or $O_2$ at a gas hourly space velocity of at least about 200 $cm^3g^{-1}h^{-1}$ at a temperature in the range of 400°–800° C. and pressure in the range of 1–5 atm for a period of at least 0.2 h, and iii) contacting the catalyst obtained in step (ii) with said $C_{1-2}$ alkane or mixture of said alkanes and at least one olefin or at least one higher paraffin or both or feed containing said alkanes, at a gas hourly space velocity in the range of 1000–100000 $cm^3g^{-1}h^{-1}$ at a temperature in the range of 300°–600° C. and pressure in the range of 1–5 atm, thereby forming a reaction mixture containing aromatics, iv) separating the aromatics formed from the reaction mixture, v) recycling unconverted alkanes and non-aromatics to step (iii).

2. A process as claimed in claim 1 wherein the inert gas used in step (i) is selected from $N_2$, Ar, and He and is present in a concentration from traces to 80 mol. %.

3. A process as claimed in claim 1 wherein the $H_2$/inert gas mole ratio employed ranges from 0.05–5.0.

4. A process as claimed in claim 1 wherein the steam/inert gas mole ratio employed ranges from 0.02–2.0.

5. A process as claimed in claim 1 wherein the feed of step (iii) comprises a $C_{2-10}$ olefin.

6. A process as claimed in claim 1 wherein the feed of step (iii) comprises a $C_{2-10}$ paraffin.

7. A process as claimed in claim 1 wherein the feed of step (iii) is natural gas containing methane and ethane.

8. A process as claimed in claim 1 wherein the bifunctional pentasil zeolite catalyst has a ZSM-5, ZSM-8 or ZSM-11 structure containing a large number of 5-member oxygen rings.

9. A process as claimed in claim 1 wherein the bifunctional pentasil zeolite is selected from a group consisting of Ga-containing ZSM-5 zeolites, Ga-impregnated H-ZSM-5, Ga-exchanged H-ZSM-5, H-gallosilicate of ZSM-5 structure and H-galloaluminosilicate of ZSM-5 structure.

10. A process as claimed in claim 1 wherein the bifunctional pentasil zeolite is H-galloaluminosilicate of ZSM-5 structure with framework (tetrahedral) Si/Al and Si/Ga mole ratio of about 10–100 and 15–150 respectively, and non-framework (octahedral) Ga of about 0.5–5.0 wt. %.

11. A process as claimed in claim 1 wherein the transition element is selected from Cr, Mo, Fe, Co, Ni, Zn, Re, Ru, Rh, Pd, Os, Ir and Pt or a mixture thereof.

12. A process as claimed in claim 1 wherein the amount of the transition element present in the catalyst ranges from traces to 10 wt. %.

13. A process as claimed in claim 1 wherein the catalyst contains a binder.

14. A process as claimed in claim 1 wherein the feed of step (iii) has a mole ratio of olefin to $C_{1-2}$ alkane or paraffin containing more than 2 carbons to $C_{1-2}$ alkane ranging from about 0.2 to about 2.0.

15. A process as claimed in claim 1 wherein the gas hourly space velocity of the feed in step (iii) ranges from about 3000 $cm^3g^{-1}h^{-1}$ to about 50,000 $cm^3g^{-1}h^{-1}$.

16. A process as claimed in claim 1 wherein the temperature employed in step (iii) ranges from 400°–600° C.

17. A process as claimed in claim 1 wherein the pressure employed in step (iii) ranges from 1 atm to 3 atm.

18. A process as claimed in claim 1 wherein said alkane of step (iii) is methane, ethane or both.

19. A process as claimed in claim 1 wherein the reaction is carried out in a single or multiple fixed bed reactor or fluid bed reactor or moving bed reactor.

20. A process as claimed in claim 1 wherein the feed of step (iii) comprises a $C_{2-4}$ olefin.

21. A process as claimed in claim 1 wherein the feed of step (iii) comprises a $C_{3-6}$ parafin.

22. A process as claimed in claim 1 wherein the zeolite catalyst has a ZSM-8 or ZSM-11 structure containing a large number of 5-member oxygen rings.

23. A process as claimed in claim 1 wherein the transition element is selected from Cr, Mo, Fe, Co, Zn, Ru, Os, and a mixture thereof.

24. A process as claimed in claim 13 wherein the binder is alumina, silica, clay, or mixtures thereof.

25. A process for the conversion of said alkanes or a feed containing said alkane(s) to aromatics, which comprises:

i) treating a bifunctional pentasil zeolite catalyst which is an H-galloaluminosilicate of ZSM-5 structure, optionally containing one or more transition elements, having strong dehydrogenation and acid sites with a mixture of $H_2$, steam and optionally the presence of an inert gas at a gas hourly space velocity of at least about 500 $cm^3g^{-1}h^{-1}$ at a temperature in the range of 400°–800° C. and pressure in the range of 1–5 atm for a period of at least 0.5 h;

ii) treating the catalyst obtained in step (i) with air or $O_2$ at a gas hourly space velocity of at least about 200 $cm^3g^{-1}h^{-1}$ at a temperature in the range of 400°–800° C. and pressure in the range of 1–5 atm for a period of at least 0.2 h and iii) contacting the catalyst obtained in step (ii) with said $C_{1-2}$ alkane or mixture of said alkanes and at least one olefin or at least one higher paraffin or both or feed containing said alkanes, at a gas hourly space velocity in the range of 1000–100000 $cm^3g^{-1}h^{-1}$ at a temperature in the range of 300°–600° C. and pressure in the range of 1–5 atm thereby forming a reaction mixture containing aromatics, iv) separating the aromatics formed from the reaction mixture, v) recycling unconverted alkanes and non-aromatics to step (iii).

* * * * *